United States Patent [19]

Riuli

[11] Patent Number: 4,713,060
[45] Date of Patent: Dec. 15, 1987

[54] SYRINGE ASSEMBLY

[75] Inventor: Arduino Riuli, Wayne, N.J.

[73] Assignee: Becton, Dickinson and Company, Franklin Lakes, N.J.

[21] Appl. No.: 876,501

[22] Filed: Jun. 20, 1986

[51] Int. Cl.⁴ .............................................. A61M 5/32
[52] U.S. Cl. ................................... 604/199; 604/218
[58] Field of Search ............... 604/111, 187, 199, 89, 604/218; 128/DIG. 18

[56] References Cited

U.S. PATENT DOCUMENTS

| | | |
|---|---|---|
| 3,905,521 | 9/1975 | Mead et al. |
| 3,957,052 | 5/1976 | Topham |
| 4,030,498 | 6/1977 | Tompkins |
| 4,185,628 | 1/1980 | Kopfer ........................... 604/89 X |

FOREIGN PATENT DOCUMENTS 84542 12/1965 France ............................ 604/199

Primary Examiner—John D. Yasko
Attorney, Agent, or Firm—John L. Voellmicke

[57] ABSTRACT

An operable syringe assembly includes a barrel having a chamber for retaining fluid. A proximal end of the barrel includes an aperture therethrough. A distal end of the barrel includes a passageway therethrough communicating with the chamber. A stopper is slidably positioned in fluid-tight engagement inside the barrel. A plunger rod, having an elongate body portion, engages the stopper to facilitate operation of the stopper. The body portion of the plunger rod extends outwardly from the proximal end of the barrel, through the aperture. A flexible cover is attached to the barrel covering the aperture and containing that portion of the body portion of the plunger rod protruding from the aperture. The cover is flexible enough and strong enough to allow movement of the plunger rod for operating the syringe without tearing. The cover acts as a barrier for helping to block the transfer of fluid and particulate matter between the chamber and the environment.

21 Claims, 8 Drawing Figures

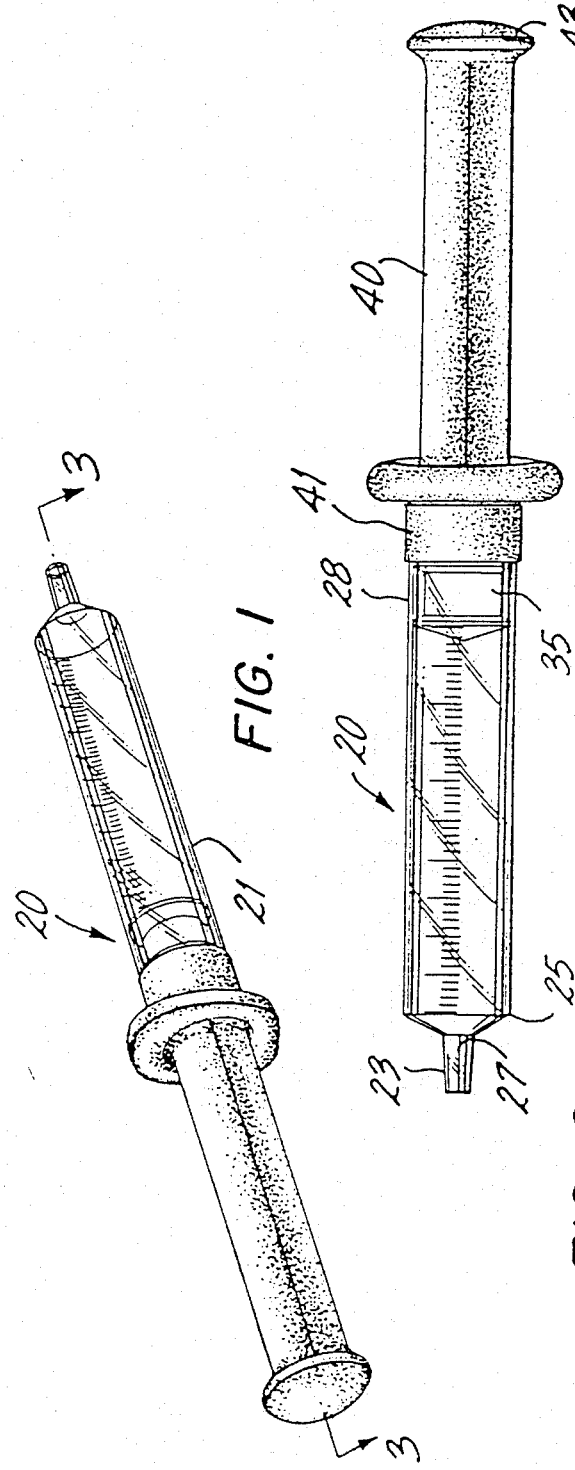
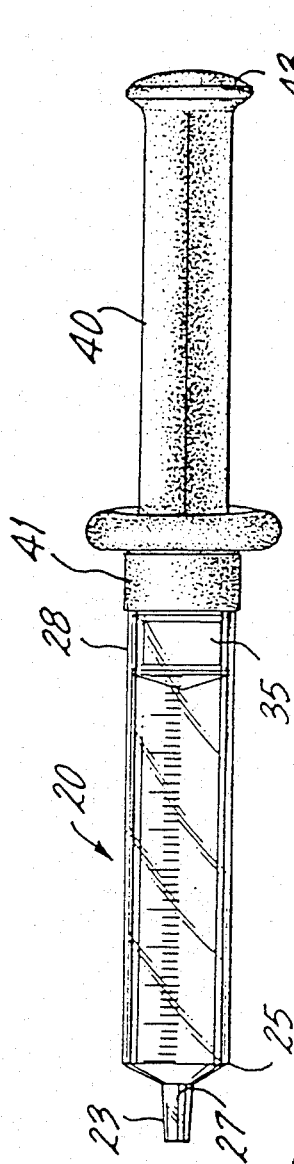
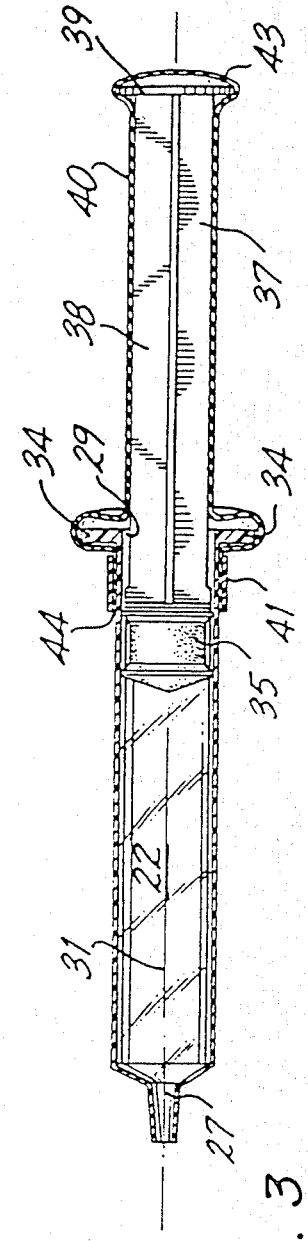
FIG. 1
FIG. 2
FIG. 3

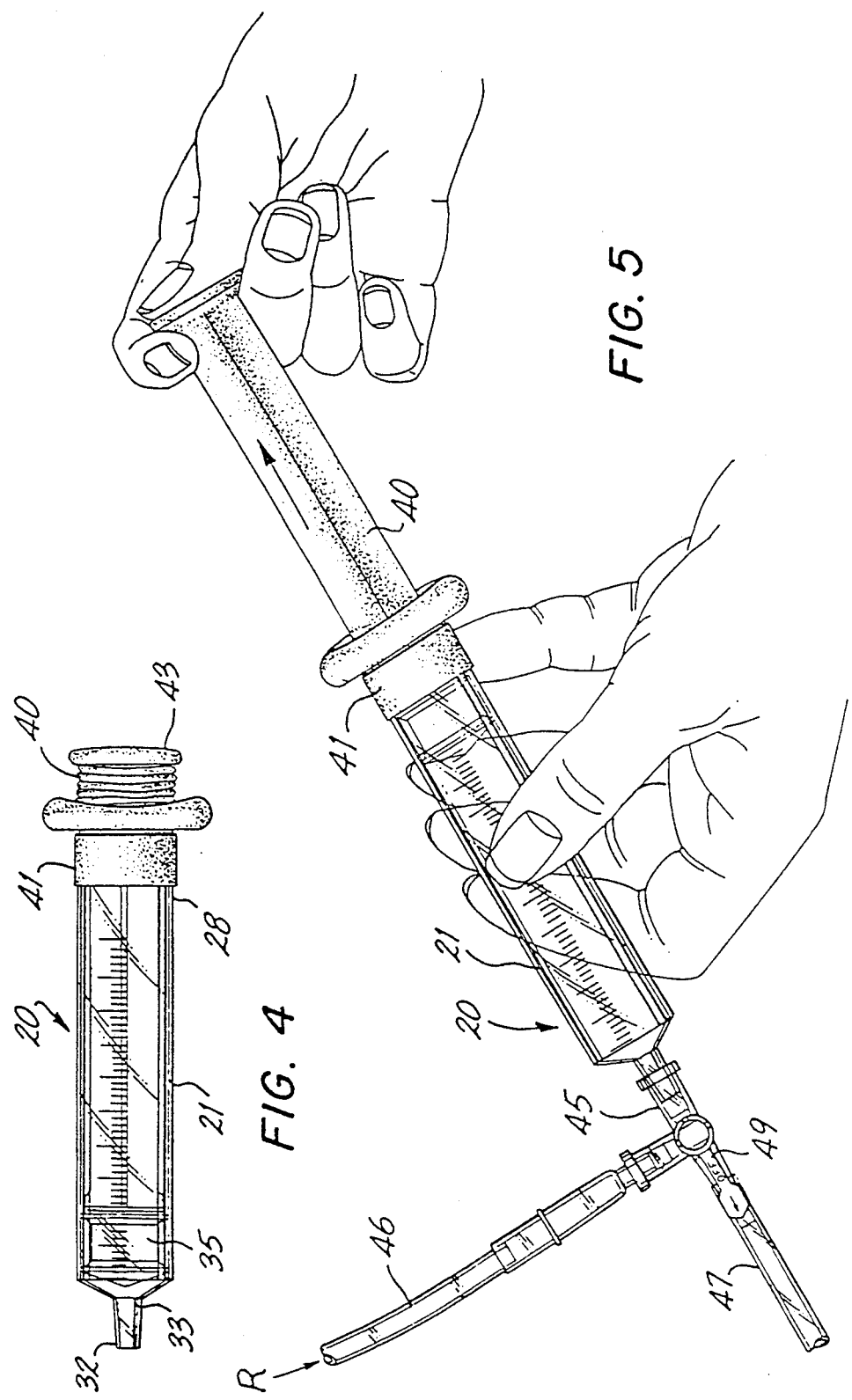

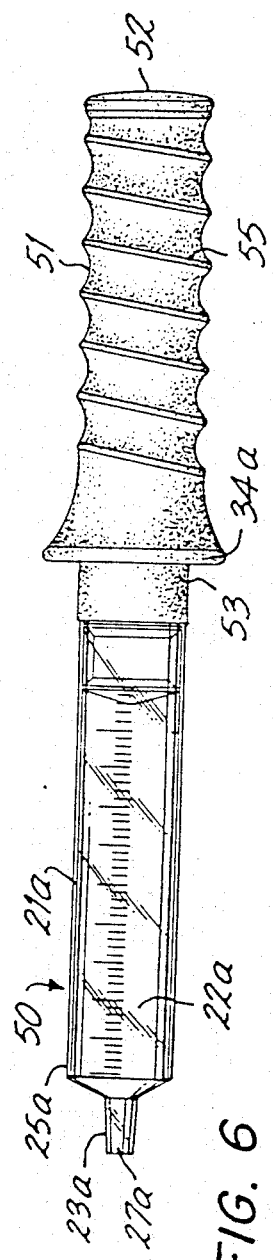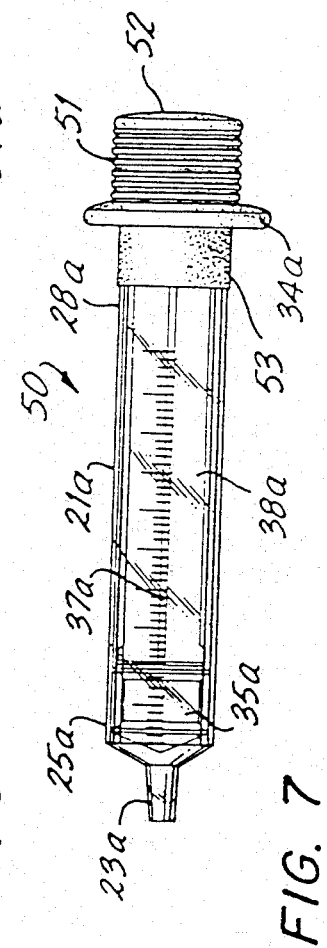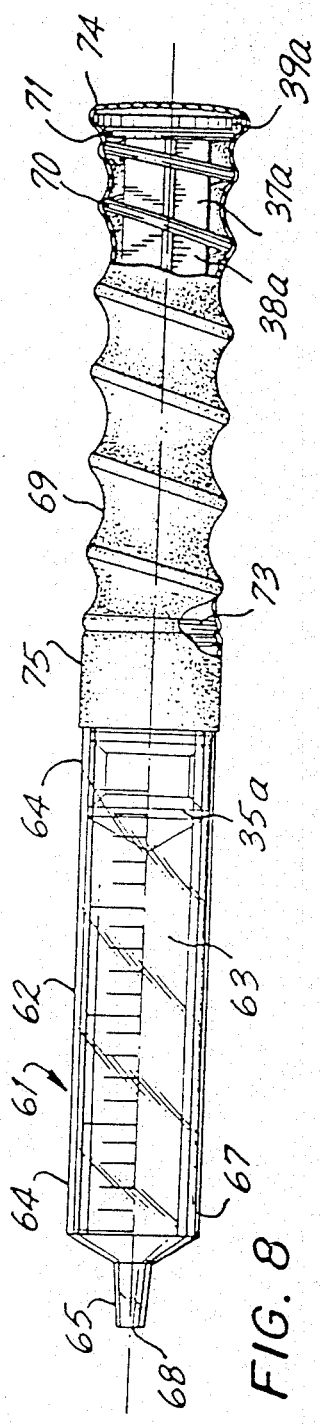

SYRINGE ASSEMBLY

BACKGROUND OF THE INVENTION

1. Field of the Invention

The present invention relates to a syringe assembly and more particularly concerns a syringe assembly having a flexible cover for blocking the transfer of fluids and particulate matter between the inside of the syringe barrel and the environment.

2. Description of Related Information

Generally speaking, a syringe assembly consists of a cylindrical barrel, most commonly made of thermoplastic material or glass, with a distal end adapted to be connected to a hypodermic needle assembly or other fluid transfer or fluid collection means. A proximal end of the barrel is adapted to receive a stopper and plunger rod assembly. One of the purposes of the stopper is to provide a relatively air-tight seal between itself and the syringe barrel so that movement of the stopper up and down the barrel will cause liquid, blood or other fluids to be drawn into or forced out of the syringe through the distal end. The stopper is moved along the syringe barrel by applying axial force to a rigid plunger rod which is connected to the stopper and is sufficiently long to be accessible outside of the barrel.

Hypodermic needle assemblies, tubing sets, stopcocks, valves and other fluid transfer devices are oftentimes removably attached to syringes for performing a variety of tasks such as: delivery of medication into patients and into devices; withdrawing fluid samples from fluid sources for subsequent delivery into a patient; and withdrawing fluid samples from patients. Usually the hub of the hypodermic needle assembly or other fluid transfer device has a tapered interior surface adapted to engage the tapered tip of the syringe barrel so that the two components are joined in a frictional interference fit. The tapered tip and the complimentary tapered receptacle and the hub are referred to as standard luer fittings. A wide variety of devices such as stopcocks and tubing sets have standard luer fittings which allow them to be engaged to a syringe tip.

Syringes may also be provided with a compression spring positioned between the proximal flange on the plunger rod and the barrel of the syringe for biasing the stopper toward the open end of the barrel. Such an arrangement is taught in U.S. Pat. No. 3,905,521 to Mead et al. Such an arrangement allows the compressed spring to provide a biasing force on the plunger rod and the stopper to create a lower than atmospheric pressure inside the barrel. This structure is useful for using the syringe as the dispenser, as taught by Mead et al., and also for using the syringe as a source of negative pressure, for example, in wound drainage setups wherein the wound is connected to the syringe through a tubing so that a lower than atmospheric pressure is constantly applied through the tubing to the wound.

Syringes are usually provided in an individual sterile package which is opened at the time of use. When the syringe is removed from the sterile package it may no longer be in a sterile environment. Accordingly, particulate matter and even bacteria in the environment may enter the syringe barrel through the proximal open end. After removal from the sterile package, a hypodermic needle assembly may be attached to the tip of the syringe barrel and then the syringe and needle assembly is used to pierce a medication vial whereupon the medication, which will be injected into the patient, is drawn into the syringe by moving the plunger rod distally with respect to the barrel. The syringe and hypodermic needle assembly are now ready to use for administering medication to the patient. Many hospitals employ drug distribution systems wherein syringes are filled with medication in the hospital pharmacy using a laminar flow hood which produces a sterile environment for the filling operation.

However, many times syringes are used in procedures wherein the plunger rod and stopper may be repeatedly drawn back and forth along the barrel while the syringe is in a non-sterile environment. Each cycling of the stopper along the barrel provides potential for contamination of the liquid contained within the syringe barrel and/or the escape of a portion of that liquid.

Syringes are often used in procedures where the syringe assembly is used as a pump or an intermediate container for liquid and the stopper is cycled many times along the syringe barrel during the procedure. This type of use of a syringe, especially in a non-sterile environment, presents an increased risk of contamination of the liquid or escape of the liquid from the stopper. Pharmacy departments in hospitals frequently draw medication from a sealed vial into a large syringe and then pump the medication from this large syringe into smaller syringes to facilitate unit dose distribution programs. Also, certain surgical procedures provide for the injection of saline solution or other therapeutic liquid into the patient's vascular or arterial system. These procedures involve a stopcock and syringe assembly wherein the syringe barrel is withdrawn to draw saline solution from a reservoir into the syringe barrel and then the position of the stopcock valve is changed so that forward motion of the stopper along the syringe barrel forces the saline solution into the patient's artery. This procedure can be repeated several times during the procedure and presents an opportunity for particulate matter in the environment to be transferred to the injecting liquid.

U.S. Pat. No. 4,030,498 to Tompkins teaches the desirability of providing structure to prevent the contamination of medication or, in the alternative, where the syringe may contain potentially hazardous substances, to prevent contamination of the user and the environment. To this end, Tompkins teaches a contamination resistant syringe having two sealing rings which are axially spaced from each other. The sealing rings are prevented from sweeping the same area, inside the syringe barrel, and there is no communication between the chamber defined by the two sealing rings and the discharge area forward of the innermost sealing ring. Tompkins teaches that, in this manner, contamination which might enter from the rear of the barrel will be prevented from contact with the inner sealing ring and therfore contact with the medication. The syringe taught by Tompkins has deficiencies in that it is more expensive to manufacture because the barrel and plunger rod must be longer than the standard plunger rod and barrel and dual sealing rings must be provided. Also, an apparently larger syringe, as taught by Tompkins, may not be compatible with the large number of syringe devices which have been developed over the period of many years to accommodate standard size syringes. Accordingly, the user may be faced with a syringe which is incompatible with the other fluid delivery equipment.

The transfer of liquid to and from the syringe assemblies and structure for making the syringe more resistant to contamination have been addressed by the prior art, as alluded to above. However, there is still a need for a simple, straight-forward, reliable, easily fabricated standard size syringe with features for helping to prevent the transfer of fluid and particulate matter between the chamber in the syringe and the environment.

SUMMARY OF THE INVENTION

A syringe assembly of the present invention comprises a barrel having a chamber for retaining fluid and a proximal end having an aperture therethrough. A distal end of the barrel includes a passageway therethrough communicating with the chamber. A stopper is slidably positioned in fluid-tight engagement inside the barrel. A plunger rod, having an elongate body portion, engages the stopper to facilitate operation of the stopper. The body portion of the plunger rod extends outwardly from the proximal end of the barrel, through the aperture. A cover means is attached to the barrel covering the aperture and containing that portion of the body portion of the plunger rod protruding from the aperture. The cover means is flexible enough and strong enough to allow movement of the plunger rod for operating the syringe without tearing the cover means. The cover means acts as a barrier for helping to block the transfer of fluid and particulate matter between the chamber and the environment.

In accordance with another embodiment of the present invention, an operable syringe assembly includes an elongate substantially cylindrical barrel having a chamber for retaining fluid. A tapered tip extends from the distal end of the barrel and includes a passageway therethrough communicating with the chamber. A flange portion projects radially outwardly from a proximal end of the barrel wherein the proximal end of the barrel includes an aperture therethrough. A stopper is slidably positioned in fluid-tight engagement inside the barrel. The stopper is capable of moving fluid from the chamber through the passageway upon its movement toward the distal end of the barrel. The stopper is also capable of facilitating the drawing of fluid into the chamber through the passageway upon its movement away from the distal end of the barrel. A plunger rod, having an elongate body portion, engages the stopper to facilitate operation of the stopper. The body portion of the plunger rod extends outwardly from the proximal end of the barrel, through the aperture. A flexible cover is attached to the barrel covering the aperture and containing that portion of the elongate body portion plunger rod protruding from the aperture. The cover is flexible enough and strong enough to allow movement of the plunger rod for operating the syringe without tearing the cover. The cover acts as a barrier for helping to block the transfer of fluid and particulate matter between the chamber and the environment through the aperture.

In accordance with the principles of the present invention, a number of advantages are achieved. Primarily, the present invention provides a simple, straightforward, reliable, easily fabricated syringe assembly with structure for helping to prevent the transfer of fluid and particulate matter between the chamber in the syringe and the environment.

BRIEF DESCRIPTION OF THE DRAWINGS

FIG. 1 is a perspective view of the preferred syringe assembly of the present invention;

FIG. 2 is a side elevation view of the preferred syringe assembly;

FIG. 3 is a partial cross-sectional view of the syringe assembly of FIG. 1 taken along line 3—3;

FIG. 4 is a side elevation view of the preferred syringe assembly illustrated with the stopper positioned at the distal end of the chamber;

FIG. 5 is a perspective view showing the user using the preferred syringe assembly in conjunction with a stopcock to transfer liquid from a reservoir to a patient;

FIG. 6 is a side elevation view of an alternative embodiment of the syringe assembly of the present invention;

FIG. 7 is a side elevation view of the embodiment of FIG. 6 illustrating the stopper positioned at the distal end of the chamber; and FIG. 8 is another alternative embodiment of the syringe assembly of the present invention.

DETAILED DESCRIPTION

While this invention is satisfied by embodiments in many different forms, there is shown in the drawings and will be herein described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 5, a syringe assembly 20, in accordance with the present invention, includes a hollow barrel 21 having a chamber 22 for retaining fluids. A tip 23 extends from a distal end 25 of the barrel and contains a passageway 27 therethrough communicating with chamber 22. A proximal end 28 of the barrel includes aperture 29 therethrough. For the purposes of the description of the present invention, the term "distal end" is meant to refer to the end furthest from the person holding the syringe barrel, whereas the term "proximal" is meant to refer to the end closest to the holder of the syringe.

Tip 23 runs along longitudinal axis 31 of the barrel and is preferably adapted to accept a known hypodermic needle assembly or adapted to engage other fluid transfer and fluid collection apparatus such as tubing sets, valves and stopcocks. Tip 23 is preferably frustoconically shaped, having a smaller outside diameter at a distal end 32 of the tip than at a proximal end 33 of the tip. It should be noted that it is within the purview of the instant invention to include syringe barrels having differently shaped distal ends including other tip shapes such as a cylindrically shaped tip having a substantially uniform outside diameter and the like. A flange portion 34 projects radially outwardly from the proximal end of the barrel.

A flexible stopper 35 is slidably positioned in fluid-tight engagement inside the barrel. The stopper is capable of moving fluid from chamber 22 through passageway 27 upon its movement toward distal end 25 of the barrel. The stopper is also capable of facilitating the drawing of fluid into the chamber through the passageway upon its movement away from distal end 25.

A plunger rod 37 includes an elongate body portion 38 engaging the stopper to facilitate operation of the stopper. The body portion of the plunger rod extends outwardly from the proximal end of the barrel, through aperture 29. A disc-shaped plunger rod flange portion 39 is preferably provided as a convenient structure for applying forces to move the plunger rod with respect to the syringe barrel. Flange portion 39 is positioned at the proximal end of elongate body portion 38 and projects radially outwardly therefrom.

A flexible cover 40 is attached to barrel 21 covering aperture 29 and containing that part of the elongate body portion of the plunger rod protruding from the aperture and flange portion 39. Cover 40 is flexible enough and strong enough to allow movement of the plunger rod for operating the syringe without tearing the cover. Cover 40 acts as the barrier for blocking the transfer of fluid and particulate matter between the chamber and the area of the environment, through the aperture. In this preferred embodiment cover 40 is mechanically held in place along the barrel via hoop-shaped member 41 which holds the cover between itself and the barrel. It is preferred that the hoop-shaped member be made of heat shrinkable plastic material and that during assembly heat is applied to the material causing the hoop-shaped member to shrink and firmly hold the cover against the outside of the barrel. Also, cover 40 may be attached to the barrel via heat sealing, adhesive or other suitable means. Further, in this preferred embodiment, the cover is an elastic tube-shaped sheath having a closed first end 43 and an open second end 44. The open second end, before assembly to the barrel, has an inside diameter which is preferably smaller than the outside diameter of the proximal end of the barrel. Accordingly, the open second end of the cover must be stretched over the barrel wherein the forces created by stretching the cover over the barrel may be sufficient to hold the cover in place during normal use of the syringe. However here, in the preferred embodiment the additional mechanical holding means of the hoop-shaped member is provided. Also, an elastic sheath can be made with a bead of integrally formed elastic material around the open second end. This additional material may provide an area of increased strength for more securely holding the sheath to the barrel when stretching the sheath over the bead in the bead area. Also, the bead may provide structure for helping to prevent the sheath from slipping out from between the hoop-shaped member and the barrel. It is within the purview of the present invention to include a structure where the plunger rod flange is outside of the cover or where the plunger rod flange may have structure to hold the first end of the cover between itself and the proximal end of the elongate body portion of the plunger rod.

It will be apparent to one skilled in the art that there are numerous means for attaching the flexible cover to a rigid barrel including heat sealing, adhesive, mechanical holding means, structure relying on the elasticity of the cover and other suitable means and that the structure described hereinabove is exemplary of these many possibilities. It is within the purview of the present invention to include a cover made of elastomeric material, as illustrated in the preferred embodiment, along with covers made of relatively inelastic flexible material such as polyethylene. The elastic material is preferred because it more closely adheres to the overall shape of the syringe assembly and does not tend to protrude outwardly or get into the way during the normal operation of the syringe.

It can be seen that the structure of the present invention provides a syringe assembly which can be operated while providing protection from the environment so that particulate matter may not enter the syringe barrel through aperture 29 or, on the other hand, particulate matter and liquid cannot leave the syringe and enter the environment even after passing through aperture 29 because the passage of this material will be blocked by flexible cover 40. The structure of the instant invention is particularly desirable in procedures where the plunger rod is moved up and down along the barrel repeatedly while the syringe is in a potentially non-sterile environment.

It can also be seen that the instant invention does not contain additional internal structure, such as a series of sealing rings on the plunger rod, as taught by the prior art. Therefore, the syringe assembly of the instant invention can be made to be approximately the same length as known syringes not having the protective features of the instant invention. Accordingly, the syringe assembly of the instant invention may, in some cases, be used with devices, such as syringe pumps, and placed in storage areas, such as in surgical procedure kits, designed for known prior art syringes.

Referring now to FIG. 5, during certain procedures, such as tests for determining cardiac output, the physician uses a syringe assembly connected to valve means such as a known three-way stopcock 45 and tubing 46 connected to a reservoir of saline solution R or other therapeutic liquid and tubing 47 connected to a catheter in the patient's arterial system. In use the physician will rotate lever 49 of the stopcock to open the passageway to tube 46. The physician then pulls the plunger rod of the syringe assembly, moving the stopper away from the distal end of the barrel, drawing saline solution from the reservoir through tube 46, through the stopcock and into the chamber. The physician then rotates lever 49 of the stopcock so that the passageway between the syringe and tube 47 is open and then the saline solution may be forced into the patient's arterial system by pressing the plunger rod so that the stopper moves toward the distal end of the syringe barrel. It can be seen with the structure of the instant invention that the cover will help eliminate the possibility of particulate matter from the surrounding environment, near the physician's hands, from entering the syringe through the aperture and eventually finding its way into the saline solution. Therefore, the physician may recycle the syringe plunger rod several times without being concerned about environmental particles entering the injectable solution. The procedure described hereinabove may also be performed with other valve means such as a two-way valve which has pressure activated one-way valves in its conduits. When using this type of two-way valves, sub-atmospheric pressure in the syringe barrel chamber causes the valves to automatically open one conduit and block the other, and above atmospheric pressure in the barrel chamber causes the one-way valves to block the previously open conduit and open the previously blocked conduit.

It can also be seen that the present invention could also act as a protective device for protecting the user from fluid within the syringe barrel that may escape around the outside of the stopper through the aperture. The present invention can be particularly useful where the fluid being handled is potentially dangerous, for example, radioactive components contained in chemotherapy solutions, or with respect to blood tests where leakage may be undesirable, for example, when handling blood containing AIDS virus.

Referring now to FIGS. 6 and 7, an alternative syringe assembly 50 of the present invention includes components which are substantially identical to the components of the embodiment of FIGS. 1–5. Accordingly, similar components performing similar functions will be numbered identically to those components in the embodiment of FIGS. 1–5, except that the suffix "a" will be used to identify the components of FIGS. 6 and 7. This alternative syringe assembly includes an elongate substantially cylindrical barrel 21a having a chamber 22a for retaining fluid. A tapered tip 23a extends from a distal end 25a of the barrel having a passageway 27a therethrough communicating with the chamber. A flange portion 34a extends radially outwardly from a proximal end 28a of the barrel. The proximal end of the barrel includes an aperture (not shown). A stopper 35a is slidably positioned in fluid-tight engagement inside the barrel. The stopper is capable of moving fluid from chamber 22a through passageway 27a upon its movement toward distal end 25a. The stopper is also capable of facilitating the drawing of fluid into the chamber through the passageway upon its movement away from the distal end of the barrel. A plunger rod 37a has an elongate body portion 38a to facilitate operation of the stopper. A portion of the body portion extends outwardly from the proximal end of the barrel, through the aperture.

A flexible cover 51 is attached to the barrel at the proximal end 28a covering the aperture and containing that portion of the plunger rod which protrudes from the aperture. The cover is made flexible enough and strong enough to allow movement of the plunger rod, for operating the syringe, without tearing the cover. The cover acts as a barrier for helping to block the transfer of fluid and particulate matter between the chamber and the environment through the aperture. In this embodiment the cover is an elastic tube-shaped sheath having a closed first end 52 and an open second end 53 wherein the open end is attached around the periphery of the proximal end of the barrel. In this embodiment the cover is constructed of elastic material, such as latex rubber or polyurethane, having a second end with a smaller inside diameter than the outside diameter of the proximal end of the barrel so that when the cover is attached to the barrel the second end of the cover is stretched over the barrel. The forces created in stretching the second end of the cover over the barrel are sufficient to hold the cover in place on the barrel during normal use of the syringe.

This embodiment also includes a support means for keeping the sheath spaced from the elongate body portion of the plunger rod so that the cover will collapse neatly, as best illustrated in FIG. 7, and not drag along the elongate body portion of the plunger rod. Here the support means is a thin, relatively weak, coil-shaped wire member 55 surrounding the plunger rod, positioned between the proximal end of the barrel and the proximal end of the plunger rod. The coil-shaped wire member is sufficiently strong to hold the cover away from the elongate portion of the plunger rod but it is not strong enough to move the plunger rod within the syringe. The primary purpose of member 55 is separating the cover from the plunger rod without substantially interfering with the operation of the syringe.

Referring now to FIG. 8, another alternative embodiment of the syringe assembly 61 of the present invention includes a hollow barrel 62 having a chamber 63 for retaining fluid. A proximal end 64 includes an aperture therethrough, a tapered tip 65 extends from distal end 67 of the barrel and includes a passageway 68 therethrough for communicating with the chamber. A stopper 35a is slidably positioned in fluid-tight engagement inside the barrel. A plunger rod 37a having an elongate body portion 38a engages the stopper to facilitate operation of the stopper. The body portion of the plunger rod extends outwardly from the proximal end of the barrel through the aperture. Cover means, in the form of a flexible cover 69 is attached to the barrel covering the aperture and containing that portion of the plunger rod protruding from the aperture. The cover is flexible enough and strong enough to allow movement of the plunger rod for operating the syringe without tearing of the cover. The cover acts as a barrier for helping to block the transfer of fluid and particulate matter between the chamber and the environment through the aperture. This alternative embodiment also includes spring means, in the form of a helical compression spring 70 having a proximal end 71 contacting disc-shaped plunger rod flange 39a and a distal end 73 contacting the proximal end of the barrel. The helical compression spring acts between the barrel and the plunger rod for biasing stopper 35a toward the proximal end of the barrel so that the syringe assembly is capable of applying suction forces through passageway 68 without external forces being applied to the syringe assembly. The cover preferably covers that portion of the spring means extending outwardly from the proximal end of the barrel. This embodiment of the present invention is particularly useful for wound drainage procedures wherein tip 65 is connected to a flexible tube (not shown) which is in turn connected to a patient's wound so that a constant suction force can be applied to the wound to facilitate drainage of fluids therefrom. In this embodiment the open end of cover 69 is attached to the proximal end of barrel 62 using an adhesive. The cover is constructed of a relatively thin flexible material, such as (0.005 inch) polyethylene sheet, in the form of a receptacle having a closed end 74 and an open end 75. Wherein the open end 75 is attached to the proximal end of the barrel via the use of an adhesive. It is within the purview of the instant invention to include a wide variety of flexible and elastic materials in the construction of the cover and a wide variety of connecting means such as adhesives, clamping means, ultrasonic welding and the like for attaching the cover to the barrel. It is also within the purview of the instant invention to include embodiments wherein the cover is positioned inside the compression spring while still covering the elongate shaft portion of the plunger rod.

The flexible cover can be constructed of a wide variety of flexible materials including plastic material, thermoplastic elastomers, natural rubber and synthetic rubber with latex rubber being desirable and polyurethane being preferred. The flexible cover the present invention can be made using a dip-molding process. The dip-molding process can be used with such materials as latex rubber to form an elastic cover having preformed areas to accept the disc-shaped flange at the end of the plunger rod and the flange portion on the proximal end of the barrel to form a neatly fitting structure which provides an effective barrier without interfering with the normal operations of the syringe.

A wide variety of rigid materials is suitable for constructing the plunger rod and the syringe barrel with plastic materials such as polypropylene, polyethylene and polystyrene being preferred.

A helical compression spring for biasing the plunger rod may be made of a wide variety of spring materials with stainless steel being preferred. Also, the coil-shaped wire member serving as a support means for the cover is preferably made of stainless steel or resilient plastic material.

The mechanical holding means, in the form of a hoop-shaped member, is preferably made of known heat-shrinkable plastic material.

Thus, it can be seen that the present invention provides a simple, straightforward, reliable, easily fabricated syringe assembly having a cover means acting as a barrier to help block the transfer offluid and particulate matter between the chamber in the syringe and the environment. The present invention also provides a syringe assembly having a spring means acting between the barrel and the plunger rod for biasing the stopper toward the proximal end of the barrel so that the syringe will be capable of applying suction forces without external forces being applied to the syringe. The present invention can also be constructed so that it is approximately the same size as known hypodermic syringes not having the protective features of the present invention so that the syringe assembly of the instant invention may, in some cases, be used with devices and placed in storage areas designed for the known prior art syringes.

What is claimed is:

1. An operable syringe assembly comprising:
   a hollow barrel having a chamber for retaining fluid;
   a proximal end of said barrel having an aperture therethrough;
   a distal end of said barrel having a passageway therethrough communicating with said chamber;
   a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end;
   a plunger rod having an elongate body portion engaging said stopper to facilitate operation of said stopper, said body portion extending outwardly from said proximal end of said barrel, through said aperture; and
   a flexible cover having a closed first end and an open second end, said open second end being attached to said barrel covering said aperture and containing that portion of said elongate body portion of said plunger rod protruding from said aperture, said covering being flexible enough and strong enough to allow movement of said plunger rod for operating said syringe without tearing, said cover acting as a barrier for helping to block the transfer of fluid and particulate matter between said chamber and the environment.

2. The syringe assembly of claim 1 further including a flange portion projecting radially outwardly from said proximal end of said barrel.

3. The syringe assembly of claim 1 wherein said cover is an elastic tube-shaped sheath, said open second end being attached around the periphery of said proximal end of said barrel.

4. The syringe assembly of claim 3 wherein said open second end of said cover has a smaller inside diameter than the outside diameter of said proximal end of said barrel before said cover is attached to said barrel, said open second end of said cover being stretched over said barrel wherein the forces created by stretching said cover over said barrel are sufficient to hold said cover in place during normal use of said syringe.

5. The syringe assembly of claim 1 wherein said cover is attached to said barrel using adhesive.

6. The syringe assembly of claim 1 further including mechanical holding means for attaching said cover to said barrel.

7. The syringe assembly of claim 6 wherein said mechanical holding means includes a hoop-shaped member positioned at said proximal end of said barrel holding said cover between itself and said barrel.

8. The syringe assembly of claim 7 wherein said hoop-shaped member is made of heat-shrinkable plastic material.

9. The syringe assembly of claim 1 further including spring means acting between said barrel and said plunger rod for biasing said stopper toward the proximal end of said barrel so that said syringe assembly is capable of applying suction forces through said passageway without external forces being applied, said cover covering that portion of said spring means extending outwardly from the proximal end of said barrel.

10. The syringe assembly of claim 9 wherein said spring means includes a helical compression spring.

11. The syringe assembly of claim 3 further including support means for keeping said sheath spaced from said elongate body portion of said plunger rod.

12. The syringe assembly of claim 11 wherein said support means includes a coil-shaped wire member surrounding said plunger rod, said wire being positioned between said proximal end of said barrel and the proximal end of said plunger rod.

13. The syringe assembly of claim 1 further including a plunge rod flange portion positioned at the proximal end of said elongate body portion of said plunger rod and projecting radially outwardly therefrom.

14. The syringe assembly of claim 1 wherein said cover is made from materials selected from the group consisting of plastic material, thermoplastic elastomers, natural rubber, and synthetic rubber.

15. The syringe assembly of claim 14 wherein said thermoplastic elastomer is polyurethane.

16. An operable syringe assembly comprising:
   an elongate substantially cylindrical barrel having a chamber for retaining fluid;
   a tapered tip extending from a distal end of said barrel having a passageway therethrough communicating with said chamber;
   a flange portion projecting radially outwardly from a proximal end of said barrel, said proximal end having an aperture therethrough;
   a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end;
   a plunger rod having an elongate body portion engaging said stopper to facilitate operation of said stopper, said body portion extending outwardly from said proximal end of said barrel, through said aperture;
   a flexible cover having a closed first end and an open second end, said open second end being attached to said barrel covering said aperture and containing that portion of said elongate body portion of said plunger rod protruding from said aperture, said cover being flexible enough and strong enough to allow movement of said plunger rod for operating said syringe without tearing, said cover acting as a barrier for helping to block the transfer of fluid and particulate matter between said chamber and the environment.

17. The syringe assembly of claim 16 wherein said cover is an elastic tube-shaped sheath, said second open end being attached around the periphery of said proximal end of said barrel.

18. The syringe assembly of claim 16 further including mechanical holding means for attaching said cover to said barrel.

19. The syringe assembly of claim 16 further including a plunger rod flange portion positioned at the proximal end of said elongate body portion of said plunger rod and projecting radially outwardly therefrom.

20. The syringe assembly of claim 16 further including spring means acting between said barrel and said plunger rod for biasing said stopper toward the proximal end of barrel so that said syringe assembly is capable of applying suction force through said passageway without external forces being applied.

21. The syringe assembly of claim 16 further including valve means removably attached to said tip so that said syringe assembly may be used for drawing fluid from a reservoir through a first tube into said chamber and then delivering said fluid through a second tube without disconnecting said tubes.

* * * * *